(12) United States Patent
Iwao et al.

(10) Patent No.: US 8,096,417 B2
(45) Date of Patent: *Jan. 17, 2012

(54) PATCH PACKAGE STRUCTURE

(75) Inventors: Yoshihiro Iwao, Ibaraki (JP); Akinori Hanatani, Ibaraki (JP); Junichi Sekiya, Ibaraki (JP); Hitoshi Akemi, Ibaraki (JP)

(73) Assignees: Nitto Denko Corporation, Osaka (JP); Sasaki Chemical Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/314,563

(22) Filed: Dec. 12, 2008

(65) Prior Publication Data

US 2009/0166236 A1     Jul. 2, 2009

(30) Foreign Application Priority Data

Dec. 14, 2007  (JP) ................................. 2007-323891

(51) Int. Cl.
*A61B 19/02* (2006.01)
*B65D 73/00* (2006.01)
*B65D 65/26* (2006.01)

(52) U.S. Cl. ........................................ 206/438; 206/484
(58) Field of Classification Search .................. 206/823, 206/484, 581, 438, 231, 321, 439, 440, 484.1, 206/484.2, 460, 210, 570, 828; 424/448, 424/449; 428/905, 354, 92.1, 475.2, 42.8, 428/475.5, 516, 520; 124/823, 484, 581, 124/438, 231; 383/210, 211
See application file for complete search history.

(56) References Cited

U.S. PATENT DOCUMENTS

| 4,657,133 | A | * | 4/1987 | Komatsu et al. | 206/204 |
| 4,861,632 | A | * | 8/1989 | Caggiano | 428/35.2 |
| 5,268,209 | A | * | 12/1993 | Hunt et al. | 428/34.3 |
| 5,505,306 | A | * | 4/1996 | Akemi et al. | 206/438 |
| 5,950,830 | A | * | 9/1999 | Trigger | 206/440 |

(Continued)

FOREIGN PATENT DOCUMENTS

JP    2001-009985    1/2001

OTHER PUBLICATIONS

U.S. Appl. No. 12/314,564 filed Dec. 12, 2008.

*Primary Examiner* — J. Gregory Pickett
*Assistant Examiner* — Andrew Perreault
(74) *Attorney, Agent, or Firm* — Wenderoth, Lind & Ponack, L.L.P.

(57) ABSTRACT

The main object of the present invention is to provide a patch package structure capable of stably retaining the physiologically active ingredient in a patch during preservation of the patch. This object can be achieved by employing the following constitution.

To be specific, the present invention is a patch package structure including a patch 1 and a packaging member 51 holding the patch, wherein the patch 1 includes a support 2 and an adhesive layer 3 formed on at least one surface of the support 2, the packaging member 51 includes a first package 11, the first package 11 including an acrylonitrile resin layer 12, a moisture-absorbing layer 13 formed on the acrylonitrile resin layer 12, and a moisture impermeable layer 14 formed on the moisture-absorbing layer 13, and the acrylonitrile resin layer 12 is provided on the proximal side of the patch 1.

16 Claims, 3 Drawing Sheets

U.S. PATENT DOCUMENTS

| | | | |
|---|---|---|---|
| 6,042,913 A * | 3/2000 | Miranda et al. | 428/40.1 |
| 6,467,621 B1 * | 10/2002 | Ishida | 206/460 |
| 6,902,817 B2 * | 6/2005 | Bowen et al. | 428/475.2 |
| 6,991,095 B1 * | 1/2006 | Yamasoto et al. | 206/204 |
| 2003/0000639 A1 * | 1/2003 | Akemi et al. | 156/272.8 |
| 2006/0000734 A1 * | 1/2006 | Ninomiya et al. | 206/438 |
| 2006/0234581 A1 * | 10/2006 | Saito et al. | 442/149 |
| 2007/0158227 A1 * | 7/2007 | Amano et al. | 206/438 |

* cited by examiner

PATCH PACKAGE STRUCTURE

TECHNICAL FIELD OF THE INVENTION

The present invention relates to a patch package structure comprising a patch and a packaging member housing the patch.

BACKGROUND OF THE INVENTION

Patch is a convenient and effective dosage form used for protection of a wound or administration of a physiologically active ingredient to living organisms. However, since its form is flat and plane and has a large surface area, the quality of patch is susceptible to influence from the environment outside the patch. Hence, the package structure thereof needs to be improved.

JP-A-2001-9985 discloses a patch package structure using a package comprising a low density polyethylene (hereinafter to be referred to as "LDPE") layer, and an LDPE layer comprising an inorganic filler dispersed therein, an aluminum foil and a high density polyethylene (hereinafter to be referred to as "HDPE") layer laminated in this order on the LDPE layer. However, such patch package structure may decrease the content of a physiologically active ingredient in the patch, since the innermost layer of the packaging member is made of LDPE, which absorbs the physiologically active ingredient. In addition, since the LDPE layer has poor rigidity, when a physical impact from the outside is applied to the packaging member, the patch easily suffers from the impact.

BRIEF SUMMARY OF THE INVENTION

In view of the above-mentioned situation, the problems to be solved by the invention include provision of a patch package structure superior in a patch protection effect against a physical impact from the outside.

In addition, they include provision of a patch package structure capable of effectively suppressing moisture absorption of an adhesive layer in the patch during preservation thereof, without producing an extremely dry preservation environment (surrounding environment of patch).

Moreover, they include provision of a patch package structure capable of stably maintaining the physiologically active ingredient in the patch during preservation thereof.

Moreover, they include provision of a patch package structure comprising a packaging member showing good heat sealability and a packaging member which is easy to produce.

To solve the above-mentioned problems, the present invention has the following constitution.
(1) A patch package structure comprising a patch and a packaging member housing the patch,
wherein
the patch comprises a support and an adhesive layer formed on at least one surface of the support,
the packaging member comprises a first package,
the first package comprises an acrylonitrile resin layer, a moisture-absorbing layer formed on the acrylonitrile resin layer, and a moisture impermeable layer formed on the moisture-absorbing layer, and
the acrylonitrile resin layer is provided on the proximal side of the patch.
(2) The patch package structure of the above-mentioned (1), wherein the packaging member further comprises a second package, one of the first package and the second package is in the form of a tray, and the other is in the form of a sheet.
(3) The patch package structure of the above-mentioned (1), wherein the packaging member further comprises a second package, and both the first package and the second package are each in the form of a sheet.
(4) The patch package structure of any of the above-mentioned (1)-(3), wherein the patch comprises a physiologically active ingredient.
(5) The patch package structure of any of the above-mentioned (1)-(4), wherein the first package further comprises a moisture permeation control layer between the acrylonitrile resin layer and the moisture-absorbing layer.
(6) The patch package structure of any of the above-mentioned (1)-(5), wherein the acrylonitrile resin is a copolymer comprising acrylonitrile as a main structural unit.
(7) The patch package structure of the above-mentioned (6), wherein the copolymer comprising acrylonitrile as a main structural unit is a copolymer comprising, as structural units, at least acrylonitrile and alkyl(meth)acrylate wherein the alkyl group has 1 to 6 carbon atoms.
(8) The patch package structure of the above-mentioned (6), wherein the copolymer comprising acrylonitrile as a main structural unit is a copolymer comprising at least acrylonitrile and butadiene as structural units.
(9) The patch package structure of the above-mentioned (6), wherein the copolymer comprising acrylonitrile as a main structural unit is a copolymer comprising, as structural units, acrylonitrile, butadiene, and alkyl(meth)acrylate wherein the alkyl group has 1 to 6 carbon atoms.
(10) The patch package structure of the above-mentioned (3), wherein the first package and the second package are substantially flat.
(11) The patch package structure of any of the above-mentioned (2)-(10), wherein
the second package comprises an acrylonitrile resin layer, a moisture-absorbing layer formed on the acrylonitrile resin layer, and a moisture impermeable layer formed on the moisture-absorbing layer, and
the acrylonitrile resin layer is provided on the proximal side of the patch.
(12) The patch package structure of the above-mentioned (11), wherein the second package further comprises a moisture permeation control layer between the acrylonitrile resin layer and the moisture-absorbing layer.
(13) The patch package structure of the above-mentioned (11) or (12), wherein the acrylonitrile resin is a copolymer comprising acrylonitrile as a main structural unit.
(14) The patch package structure of the above-mentioned (11) or (12), wherein the copolymer comprising acrylonitrile as a main structural unit is a copolymer comprising, as structural units, at least acrylonitrile and alkyl(meth)acrylate wherein the alkyl group has 1 to 6 carbon atoms.
(15) The patch package structure of the above-mentioned (11) or (12), wherein the copolymer comprising acrylonitrile as a main structural unit is a copolymer comprising at least acrylonitrile and butadiene as structural units.
(16) The patch package structure of the above-mentioned (11) or (12), wherein the copolymer comprising acrylonitrile as a main structural unit is a copolymer comprising, as structural units, acrylonitrile, butadiene, and alkyl(meth)acrylate wherein the alkyl group has 1 to 6 carbon atoms.

The physiologically active ingredient in the patch does not easily permeate through an acrylonitrile resin layer, and is not easily adsorbed by the acrylonitrile resin layer. Therefore, since an acrylonitrile resin layer is disposed on the proximal side of a patch in the patch package structure of the present invention, when the patch contains a physiologically active ingredient, a decrease in the content thereof can be suppressed.

In addition, the moisture in the environment inside the patch and the packaging member permeates through an acrylonitrile resin layer and is absorbed by a moisture-absorbing layer. The moisture impermeable layer substantially blocks the moisture transfer. Hence, decomposition of a physiologically active ingredient in the patch by moisture is suppressed, and a decrease in the content due to the decomposition can also be suppressed.

According to the present invention, therefore, when the patch contains a physiologically active ingredient, it is possible to suppress not only a decrease in the content of a physiologically active ingredient in the patch, but also a decrease in the content due to the decomposition. Consequently, stable retention of a physiologically active ingredient in the patch during preservation thereof can be achieved at an extremely high level. Furthermore, it is possible to suppress degradation of transdermal absorbability due to alteration of a physiologically active ingredient in the patch due to water. In addition, the present invention can effectively suppress alteration of adhesive property of an adhesive layer and alteration of properties such as solubility of a physiologically active ingredient, and the like, due to moisture absorption, thus ensuring maintenance of desired properties.

Particularly using, as an acrylonitrile resin, a copolymer comprising acrylonitrile, and a rubber component (e.g., butadiene and the like) and/or an alkyl(meth)acrylate component wherein the alkyl group has 1 to 6 carbon atoms, since the copolymer simultaneously shows suitable flexibility and rigidity, a patch package structure superior in a patch protective effect against a physical impact from the outside during preservation of the patch can be realized. Moreover, since the copolymer has a lower melting point than that of polyacrylonitrile and shows extremely good heat sealability, a patch package structure comprising a package showing good heat sealability and a packaging member which is easy to produce can be realized.

BRIEF DESCRIPTION OF THE DRAWING

FIG. 4 is a schematic view of an exemplary package structure of the present invention, where FIG. 4(a) is a perspective view and FIG. 4(b) is a sectional view of FIG. 4(a) along the line B-B.

FIG. 5 is a schematic view of an exemplary package structure of the present invention, where FIG. 5(a) is a perspective view and FIG. 5(b) is a sectional view of FIG. 5(a) along the line B-B.

In the Figures, 1 is a patch, 2 is a support, 3 is an adhesive layer, 4 is a release liner, 11 is the first package, 12 is an acrylonitrile resin layer, 13 is a moisture-absorbing layer, 14 is a moisture impermeable layer, 15 is the second intermediate layer, 16 is the first intermediate layer, 21 is the second package, 51 is a pouch-like packaging member, and 52 is a blister-like packaging member.

DETAILED DESCRIPTION OF THE INVENTION

The present invention is explained in the following by referring to a preferable embodiment.

The patch package structure of the present invention comprises a patch and a packaging member housing the patch. The packaging member comprises a package having a laminate structure consisting of an acrylonitrile resin layer/moisture-absorbing layer/moisture impermeable layer. The acrylonitrile resin layer is provided on the proximal side of the patch.

[Patch]

Figure 1:
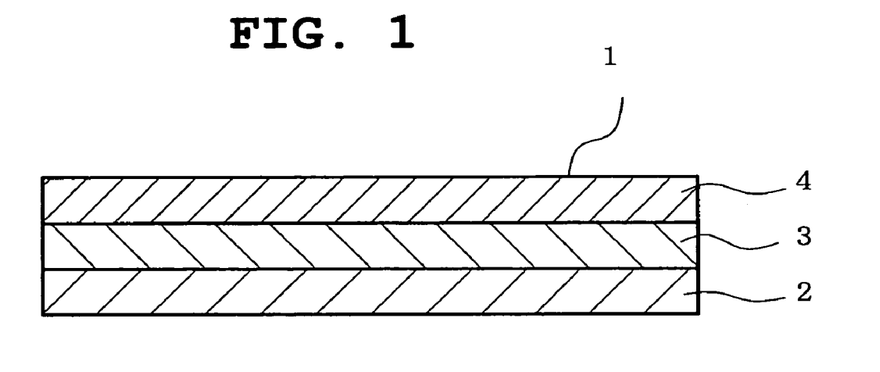
FIG. 1 is a schematic sectional view of an exemplary patch to be used in the present invention.

In the present invention, the "patch" is, for example, a product having at least an adhesive layer, which is used by applying to the skin of human and animals for the protection of a wound or administration of a physiologically active ingredient to living body(s). While the form thereof is not particularly limited, it is typically a structure having a support 2, an adhesive layer 3 provided on at least one surface of the support 2, and, where necessary, a release liner 4 to protect the surface of the adhesive layer 3, as shown by a patch 1 in one embodiment shown in FIG. 1.

While the support is not particularly limited, one substantially impermeable to a drug and the like, in other words, one that does not permit a decrease in the content of a drug, an additive and the like in the adhesive layer, which may be lost from the back face through the support, is preferable. Examples of such support include a film made of polyester, nylon, saran (registered trade mark), polyethylene, polypropylene, poly(vinyl chloride), ethylene-ethyl acrylate copolymer, polytetrafluoroethylene, Surlyn (registered trade mark), metal foil or the like, a laminate film thereof and the like. The thickness of the support is generally 10-500 μm, preferably 10-200 μm.

The adhesive to be used for the adhesive layer is not particularly limited as long as it has skin adhesiveness. Specific examples thereof include acrylic adhesives comprising acrylic polymer; rubber adhesives such as styrene-diene-styrene block copolymer (e.g., styrene-isoprene-styrene block copolymer, styrene-butadiene-styrene block copolymer etc.), polyisoprene, polyisobutylene, polybutadiene and the like; silicone adhesives such as silicone rubber, silicone comprising dimethylsiloxane as a main component, silicone comprising diphenylsiloxane as a main component, and the like; vinyl ether adhesives such as poly(vinyl methyl ether), poly(vinyl ethyl ether), poly(vinyl isobutyl ether) and the like; vinyl ester adhesives such as vinyl acetate-ethylene copolymer and the like; polyester adhesives comprising carboxylic acid component such as dimethyl terephthalate, dimethyl isophthalate, dimethyl phthalate and the like and polyvalent alcohol component such as ethylene glycol etc. and the like. These adhesives may be used any of one kind or a mixture of two or more kinds.

Among these adhesives, acrylic adhesives are preferable since they are easily crosslinkable, can be retained in an adhesive layer containing a large amount of a liquid component, and can produce a soft feeling of the adhesive layer upon adhesion to the skin. In addition, when the adhesive layer contains a physiologically active ingredient mentioned below, a rubber adhesive is preferable from the aspect of stability of the physiologically active ingredient. Furthermore, to more effectively utilize the moisture absorbability of the moisture-absorbing layer in the below-mentioned packaging member and to stabilize a physiologically active ingredient when the adhesive layer contains the physiologically active ingredient, preferred is an adhesive layer formed from a nonaqueous adhesive substantially free of water. Being "substantially free of water" means that water is intentionally excluded during the production step, and does not mean that the moisture naturally absorbed by an adhesive layer during exposure to the air is also excluded.

Of acrylic adhesives, from the aspect of easily adhesiveness to human skin and repeat of detach, preferably is a polymer obtained by polymerizing alkyl(meth)acrylate in the proportion of 40 wt % or more, particularly preferably a copolymer obtained by copolymerizing one or more kinds of alkyl(meth)acrylate in the proportion of 50-98 wt % and one or more kinds of copolymerizable monomer in the proportion of 2-50 wt %.

Examples of such alkyl(meth)acrylate include esters obtained from a primary, secondary or tertiary alcohol wherein the alkyl group has 2 to 18 carbon atoms, preferably 4 to 12 carbon atoms, and acrylic acid or methacrylic acid.

Examples of the copolymerizable monomer include monomers having, in the molecule, at least one unsaturated double bond involving copolymerization reaction, and having, in the side chain, a function group such as a carboxyl group (e.g., (meth)acrylic acid, itaconic acid, maleic acid, maleic anhydride etc.), a hydroxyl group (e.g., hydroxyethyl (meth)acrylate, hydroxypropyl(meth)acrylate etc.), a sulfo group (e.g., styrenesulfonic acid, allyl sulfonic acid, sulfopropyl(meth) acrylate, (meth)acryloyloxynaphthalenesulfonic acid, acrylamidomethylpropanesulfonic acid etc.), an amino group (e.g., aminoethyl(meth)acrylate, dimethylaminoethyl (meth) acrylate, tert-butylaminoethyl(meth)acrylate etc.), an amide group (e.g., (meth)acrylamide, dimethyl(meth)acrylamide, N-butylacrylamide, N-methylol(meth)acrylamide, N-methylolpropane(meth)acrylamide etc.), an alkoxyl group (e.g., methoxyethyl(meth)acrylate, ethoxyethyl(meth)acrylate, (meth)acrylic acid methoxyethyleneglycol ester, (meth) acrylic acid methoxydiethyleneglycol ester, (meth)acrylic acid methoxypolyethylene glycol ester, (meth)acrylic acid methoxypolyethylene glycol ester, tetrahydrofurfuryl (meth) acrylate etc.) and the like.

Besides the above-mentioned monomer, (meth)acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam, vinyloxazole, vinylmorpholine and the like can be used as a copolymerizable monomer.

One or more kinds of such copolymerizable monomers can be copolymerized. From the aspects of adhesiveness and cohesiveness as adhesion properties, releaseability of the physiologically active ingredient contained in an adhesive layer and the like, it is preferable to copolymerize, as an essential component, 1-50 wt %, preferably 2-20 wt %, of at least one kind from carboxyl group-containing monomers and hydroxyl group-containing monomers and, where necessary, copolymerize 40 wt % or less, preferably 30 wt % or less, of other monomer exemplified above, for example, vinyl monomers such as vinyl acetate and N-vinyl-2-pyrrolidone.

In addition, the above-mentioned rubber adhesive is preferably a rubber adhesive containing at least one selected from polyisobutylene, polyisoprene and styrene-diene-styrene block copolymer as main component. Particularly, when the physiologically active ingredient is contained in the adhesive layer, an adhesive containing a high molecular weight polyisobutylene having a viscosity average molecular weight of 500,000-5,500,000 and a low molecular weight polyisobutylene having a viscosity average molecular weight of 10,000-200,000 at weight ratio of 95:5-5:95 is particularly preferable from the aspects of high stability of the physiologically active ingredient and simultaneous provision of the necessary adhesiveness and cohesion strength.

The viscosity average molecular weight here is obtained by calculating Staudinger Index ($J_0$) from the flow time of capillary of a Ubbelohde viscosimeter at 20° C. according to the Schulz-Blaschke equation (the following formula (I)), and from the following formula (II) by inserting the obtained $J_0$ value:

$$J_0 = \eta_{sp}/c(1+0.31\eta_{sp}) \qquad \text{formula (I)}$$

wherein $\eta_{sp} = t/t_0 - 1$ t: flow time of solution (by Hagenbach-couette Correction formula)

$t_0$: flow time of solvent (by Hagenbach-couette Correction formula)

c: concentration of solution (g/cm³)

$$J_0 = 3.06 \times 10^{-2} M v^{0.65} \qquad \text{formula (II)}$$

wherein Mv: viscosity average molecular weight

When a rubber adhesive is used for the adhesive layer, a tackifier can be added to impart good tackiness to the adhesive layer. Examples of the tackifier include petroleum resins (e.g., aromatic petroleum resins, aliphatic petroleum resins), terpene resins, rosin resins, coumarone-indene resins, styrene resins, hydrogenated petroleum resins (e.g., alicyclic saturated hydrocarbon resins) and the like. Of these, an alicyclic saturated hydrocarbon resin is preferable since good preservation stability of the physiologically active ingredient can be achieved. The tackifier can be used alone or in combination. When they are used in combination, for example, a combination of different kinds of resins or resins having different softening points may be used. The content of the tackifier is preferably 15-55 wt %, more preferably 20-50 wt %, relative to the whole weight of the adhesive layer. When the content of the tackifier is less than 15 wt %, the tackiness and cohesion strength sometimes become insufficient. On the other hand, when the content exceeds 55 wt %, the adhesive layer tends to become stiff to consequently degrade the skin adhesiveness.

In the present invention, the thickness of the adhesive layer in a patch varies depending on the application site of the patch to a mammal such as human and the like, the kind of the physiologically active ingredient when a physiologically active ingredient is contained in the adhesive layer and the like. It is, in general, preferably about 10-200 μm, particularly preferably about 15-150 μm.

In the present invention, the adhesive layer can contain various physiologically active ingredients. Preferred is one that can be administered to mammals such as human and the like through the skin thereof, namely, a transdermally absorbable physiologically active ingredient. Specific examples thereof include general anesthetic drug, hypnotic sedative drug, antiepileptic drug, anti-pyretic and anti-inflammatory analgesic drug, seasick remedy, psychoneurotic drug, local anesthetic, skeleton muscle relaxant, autonomic nervous system drug, spasmolytic drug, antiparkinsonian drug, antihistamine drug, cardiac stimulant, antiarrhythmic drug, diuretic drug, hypotensive drug, vasoconstrictor, coronary vasodilator, peripheral vasodilator, anti-arteriosclerotic drug, cardiovascular drug, respiratory stimulant, antitussive and expectorant drug, hormonal drug, external medicine for purulent disease, analgesic•antipruritic•astringent•anti-inflammatory drug, drug for parasitic dermatic disease, haemostatic drug, gout remedy, diabetes drug, antineoplastic drug, antibiotic, chemotherapeutic drug, narcotic drug, stop smoking aid and the like.

The present invention is particularly advantageous when the physiologically active ingredient is a "moisture sensitive physiologically active ingredient". Here, the "moisture sensitive physiologically active ingredient" means the physiologically active ingredient which easily undergoes alteration (hydrolysis, transesterification reaction etc.) in the presence of moisture and the physiologically active ingredient which easily forms a hydrate in the presence of moisture.

Examples of the physiologically active ingredient moiety which easily undergoes hydrolysis in the presence of moisture include an ester group, an amide group, an imide group, a Schiff base and the like. Examples of the physiologically active ingredient moiety which easily undergoes transesterification reaction in the presence of moisture include an ester group, a carboxyl group, a primary or secondary amino group and the like. Note that "scopolamine" is a physiologically active ingredient having both a structure moiety which easily undergoes hydrolysis in the presence of moisture and a structure moiety which easily undergoes transesterification reaction.

The physiologically active ingredient moiety which easily forms a hydrate in the presence of moisture can be detected as a physiologically active ingredient having an inflection point in weight change under increasing relative humidity, when the physiologically active ingredient of an anhydride is measured by a gravimetric water vapor sorption analyzer. Such physiologically active ingredient moiety which easily forms a hydrate in the presence of moisture may allow precipitation of hydrate crystal in the adhesive layer, thus decreasing the releaseability of the physiologically active ingredient. Specific examples of such physiologically active ingredient moiety which easily forms a hydrate in the presence of moisture include "estradiol" and the like.

The content of a physiologically active ingredient is not particularly limited as long as it provides the effect of the physiologically active ingredient and is within the range that does not impair the adhesive property of the adhesive. It is preferably contained in the adhesive layer in a proportion of 0.1-70 wt %, more preferably 0.5-65 wt %. When the content is less than 0.1 wt %, a therapeutic or prophylactic effect may not be sufficient, and when it exceeds 70 wt %, skin irritation may be developed and the economical aspect may become disadvantageous.

In the present invention, the adhesive layer of a patch may contain various additives. Examples of such additive include an organic liquid component, a stabilizer, a filler and the like, which are preferably hydrophobic for the compatibility with the adhesive.

An organic liquid component can plasticize an adhesive, adjust adhesion to an application site, and control the transdermal absorbability of the physiologically active ingredient that can be contained in the adhesive layer. Examples of the organic liquid component include plasticizers such as diisopropyl adipate, diacetyl sebacate and the like; glycols such as ethylene glycol, diethylene glycol, propylene glycol, triethylene glycol, polyethylene glycol, poly(propylene glycol) and the like; fats and oils such as olive oil, castor oil, squalene, lanolin and the like; hydrocarbons such as liquid paraffin; various surfactants; alcohols such as polyvalent alcohols (e.g., glycerol and the like), monoalcohols (e.g., octyldodecanol, oleyl alcohol, ethoxylated stearyl alcohol and the like) and the like; glycerol esters such as glycerol monoesters (e.g., oleic acid monoglyceride, caprylic acid monoglyceride, lauryl acid monoglyceride), glycerol diesters, glycerol trimesters and a mixture thereof; fatty acid esters such as ethyl laurylate, isopropyl myristate, isotridecyl myristate, octyl palmitate, isopropyl palmitate, ethyl oleate and isopropyl adipate; fatty acids such as oleic acid and caprylic acid; N-methylpyrrolidone; 1,3-butanediol; and the like. Of these, alcohols, glycerol esters and fatty acid esters are preferable in view of the transdermal absorbability of the physiologically active ingredient.

[First Package]

Figure 2:
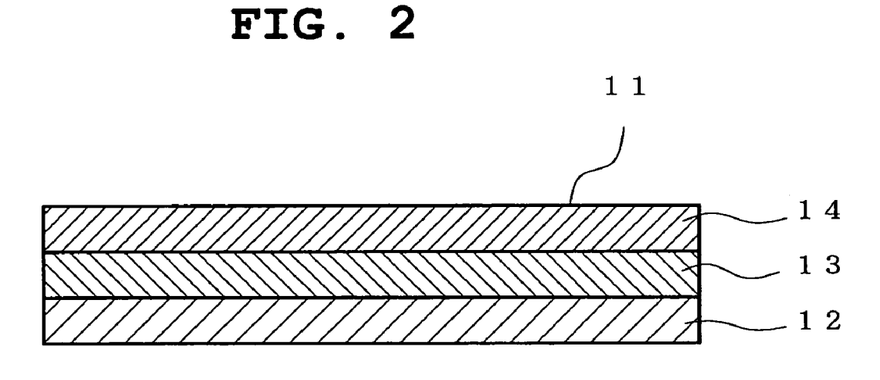
FIG. 2 is a schematic sectional view of an exemplary first package to be used in the present invention.

The packaging member of the present invention is constituted with at least the first package having a laminate structure as shown in FIG. 2. The first package 11 is a multi-layer structure containing at least an acrylonitrile resin layer 12, a moisture-absorbing layer 13 formed on the acrylonitrile resin layer 12, and a moisture impermeable layer 14 formed on the moisture-absorbing layer 13. For example, as is a packaging member 51 in the embodiment shown in the below-mentioned FIG. 4, it is used with the acrylonitrile resin layer 12 disposed on the proximal side of a patch 1. In other words, the acrylonitrile resin layer 12 constitutes the inside of the packaging member.

(Acrylonitrile Resin Layer)

An acrylonitrile resin layer 12 affords sufficient moisture permeability to the first package 11, which enables moisture absorption by the below-mentioned moisture-absorbing layer 13. In addition, when a patch contains a physiologically active ingredient, the layer 12 renders the first package 11 impermeable to the physiologically active ingredient. Here, the impermeability of the physiologically active ingredient means that the physiologically active ingredient does not substantially permeate, where permeation of an ultratrace amount of the physiologically active ingredient is acceptable as long as the physiologically active action of the physiologically active ingredient in the patch can be sufficiently obtained. For sufficient expression of the effect of the invention by the acrylonitrile resin layer, the moisture permeation rate of the acrylonitrile resin layer 12 is preferably 40-100 $g/m^2/24$ hr, more preferably 50-90 $g/m^2/24$ hr. The "water vapor transmission rate" in the present specification refers to a value obtained by the following formula (1) when, according to the Water Vapor Transmission Rate Test method defined in JIS Z 0208 (1976), a moisture permeation cup containing anhydrous calcium chloride is tightly sealed with a sample film (moisture permeation area: 28.274 $cm^2$), and the weight is measured while maintaining the outside temperature at 40° C. and relative humidity at 90% for one to several days.

$$\eta = 240 \times m/t/S \tag{1}$$

wherein $\eta$ is a water vapor transmission rate ($g/m^2/24$ hr), S is an area ($cm^2$) of moisture permeation, t is time (hr) of weighing period, and m is a mass (mg) which increased during the weighing period (time t (hr)).

The water vapor transmission rate of the acrylonitrile resin layer can be adjusted by, for example, changing the film thickness, draw ratio of the film and the like.

As mentioned below, the packaging member of the present invention is produced, for example, by surrounding a patch with a package, and heat sealing the marginal of the package. Desirably, therefore, the acrylonitrile resin layer in the first package is imparted with the heat sealability.

In the present invention, an acrylonitrile resin to be used for the acrylonitrile resin layer 12 is not particularly limited as long as the acrylonitrile component constitutes 50 wt % or more of the total weight of the resin in the layer. Accordingly, examples of the acrylonitrile resin include (i) polyacrylonitrile, (ii) a mixture or polymer alloy of polyacrylonitrile and the other resin, (iii) a copolymer wherein the main structural unit consists of acrylonitrile, or (iv) a composition obtained by combining at least two of the aforementioned (i)-(iii), and the like. From the aspects of suitable flexibility, rigidity and heat sealability as a package of a patch, one of the abovementioned (ii)-(iv) is preferable.

Acrylonitrile makes it difficult for an organic liquid component to adsorb to an acrylonitrile resin layer, imparts gas barrier property to the acrylonitrile resin layer, as well as easy-to-tear property by adding rigidity. In addition, when a patch contains a physiologically active ingredient, acrylonitrile makes it difficult for the physiologically active ingredient to adsorb to or permeate through an acrylonitrile resin layer. Therefore, the acrylonitrile resin may be entirely constituted with an acrylonitrile component. However, to afford elasticity, impact resistance, tensile strength and the like desirable as a packaging member, the resin preferably contains not less than 50 wt % of an acrylonitrile component, a rubber component such as butadiene and the like and/or an alkyl(meth)acrylate component wherein the alkyl group has 1 to 6 carbon atoms and the like. The rubber component imparts impact absorbability and appropriate flexibility to an acrylonitrile resin, and the alkyl (meth)acrylate component decreases the melting point of an acrylonitrile resin layer to improve heat sealability. In the alkyl(meth)acrylate wherein the alkyl group has 1 to 6 carbon atoms, the alkyl group may be a straight chain or branched, and one or more kinds thereof can be used. Preferable examples include methyl acrylate, methyl methacrylate, ethyl acrylate, ethyl methacrylate, (1- or 2-)propyl acrylate, (1- or 2-)propyl methacrylate, (1- or 2-)butyl acrylate, (1- or 2-)butyl methacrylate and the like. Of these, from the point of high utility and easily obtainable of flexibility as package of patch, methyl acrylate is particularly preferable.

The acrylonitrile resin is preferably a copolymer comprising acrylonitrile as a main structural unit to afford uniform property of the acrylonitrile resin layer 12. The copolymer preferably comprises, as structural units, at least acrylonitrile, and a rubber component such as butadiene and the like and/or alkyl(meth)acrylate wherein the alkyl group has 1 to 6 carbon atoms. In this copolymer, the content of acrylonitrile is preferably 50-90 wt %, and a particularly preferable copolymer composition is 50-90 wt % of acrylonitrile, 2-12 wt % of a rubber component such as butadiene and the like, and 8-38 wt % of alkyl(meth)acrylate wherein the alkyl group has 1 to 6 carbon atoms. The type of copolymerization of the copolymer is not particularly limited, and it may be random, block or graft. However, graft copolymerization is preferable since the characteristics of polyacrylonitrile showing superior non-adsorbability of the physiologically active ingredient, and the characteristics of a rubber component having superior impact absorbability can be efficiently combined. As long as such characteristics are not inhibited, random or block may be added as appropriate.

In the present invention, the composition analysis of the acrylonitrile resin is performed by the following method.

An acrylonitrile resin layer is scraped from a package to give a sample, which is subjected to an ultimate analysis of CHN, and the acrylonitrile content is calculated from the nitrogen content. Moreover, the $^1$H-NMR and $^{13}$C-NMR (in deuterated DMSO, 80° C.) spectra, and the molecule structure and weight ratio of the rubber component and alkyl (meth)acrylate wherein the alkyl group has 1 to 6 carbon atoms component are measured, and the weight ratio of the 3 component is determined.

The thickness of an acrylonitrile resin layer 12 is appropriately set according to the kind of patch and the like and is not particularly limited. However, it is preferably 10-100 μm, more preferably 10-80 μm, and most preferably 10-50 μm, since the impermeability and non-adsorbability of the physiologically active ingredient in the patch are sufficiently exhibited and appropriate flexibility and rigidity of a patch package can be ensured while retaining moisture permeability.

(Moisture Absorbable Layer)

In the present invention, the moisture-absorbing layer 13 to be formed on the acrylonitrile resin layer 12 is not particularly limited as long as it has moisture absorbability. Conveniently, a film-like molded product formed from a composition containing a moisture-absorbing agent and a resin component is used. The content of the moisture-absorbing agent is preferably 15-60 wt %, more preferably 20-40 wt %, relative to the whole composition. When the content ratio of the moisture-absorbing agent is less than 15 wt %, the environment inside the packaging member may be unsuitable for the preservation of a patch. On the other hand, when the content ratio of the moisture absorbing agent exceeds 60 wt %, the tight-sealing property may be difficult to maintain during tight sealing of the package by heat sealing.

The moisture-absorbing agent may be any of organic moisture-absorbing agents and inorganic moisture-absorbing agents. From the aspects of heat and/or chemical stability, resin processing temperature and the like, an inorganic moisture-absorbing agent is preferable. In other words, generally, from the aspects of dispersibility of moisture-absorbing agent, resin processability and the like, the resin processing temperature is generally about 100° C. to 300° C. While the organic absorption agent is sometimes decomposed or degraded, the inorganic moisture-absorbing agent is stable even in such temperature range. Preferable examples of the inorganic moisture-absorbing agent include oxides such as calcium oxide, aluminum oxide, magnesium oxide, silicon oxide (silica gel) and the like, metal salts such as calcium carbonate, magnesium sulfate and the like, and the like. Zeolite and the like can also be used. They may be in the form of any of hydrate and anhydride. In addition, when a patch containing the physiologically active ingredient is placed under an extremely dry state, there is a possibility, depending on the kind of the physiologically active ingredient, that the physiologically active ingredient or the adhesive layer are denatured, the physiologically active ingredient precipitates as crystals in the adhesive layer, and further, the transdermal absorbability of the physiologically active ingredient and the adhesiveness of the adhesive layer are degraded and the liner is detached insufficiently. Therefore, the above-mentioned moisture-absorbing agent is preferably magnesium sulfate, since it can provide a packaging member inner environment suitable for a patch without producing an extremely dry state, and is superior in the handling property. The environment inside the packaging member can be easily controlled to the equilibrated humidity optimal for the quality maintenance of the patch by, for example, kneading magnesium sulfate with polyolefin such as low density polyethylene (LDPE) and the like to form a moisture-absorbing layer. While magnesium sulfate is often used in the form of a hydrate, one having a small hydration number is preferable, since the packaging member absorbs moisture.

Such moisture-absorbing agent, particularly an inorganic moisture absorption agent is generally used in the form of a powder. The average particle size is preferably within the range of 1-40 μm, more preferably 1-20 μm, most preferably 2-10 μm. When the average particle size is less than 1 μm, kneading with and dispersion in the resin becomes strikingly difficult, rendering the processing cost unrealistic, and when the average particle size exceeds 40 μm, the smoothness and appearance of the surface of the moisture-absorbing layer may be adversely influenced, and the degree of freedom of design of the thickness of the moisture-absorbing layer may be restricted. The average particle size here means an "average volume diameter", which is an average volume diameter (MV value) measured by Microtrac particle size distribution measurement apparatus (manufactured by NIKKISO Co., LTD, MT3300EX II).

On the other hand, the resin component is not particularly limited, and, for example, polyolefin resins such as low density polyethylene (LDPE), polypropylene, ethylene-vinyl acetate, ethylene-methyl acrylate and the like are preferable. Particularly, LDPE is preferable since a moisture-absorbing layer superior in the uniform dispersibility of the moisture-absorbing agent can be formed. In addition, since LDPE is superior in the moisture permeability, the moisture that permeated through an acrylonitrile resin layer easily penetrates into the moisture-absorbing layer. As a result, water molecules and the moisture-absorbing agent inside the moisture-absorbing layer frequently come into contact with each other, thus facilitating moisture absorption by the moisture-absorbing agent. The "low density polyethylene (LDPE)" in the present invention is a polyethylene having a specific gravity $\rho(g/cm^3)$ of not less than 0.91 and less than 0.94.

The thickness of a moisture-absorbing layer 13 can be appropriately determined according to the kind of patch and the like. To achieve sufficiently high moisture absorbability as well as toughness and easy-to-open property as a package of a patch, it is preferably 10-80 μm, more preferably 10-50

(Moisture Impermeable Layer)

In the present invention, a moisture impermeable layer 14 formed on the moisture-absorbing layer 13 mainly aims to block contact of a patch with the outside air. As used herein, the "moisture impermeability" means that the moisture is not substantially permeated, and allows permeation of an ultratrace, practically acceptable amount of moisture. To sufficiently express the effect of the present invention by forming a moisture impermeable layer 14, the water vapor transmission rate of the moisture impermeable layer 14 is preferably 0-10 $g/m^2/24$ hr, more preferably 0-5 $g/m^2/24$ hr, more preferably 0-3 $g/m^2/24$ hr. The material is not limited as long as it shows such preferable moisture impermeability, and the material of the moisture impermeable layer 14 may be one used for known packages and the like. Specific examples include metal foils of, for example, aluminum and the like; a film of resins such as polyester (e.g., poly(ethylene terephthalate) (PET) and the like), high density polyethylene (HDPE), polypropylene, polyamide (nylon), vinyl chloride, vinylidene chloride, ethylene-vinyl alcohol copolymer, ethylene-vinyl acetate and the like; a vapor deposition film obtained by vapor-depositing a metal such as aluminum and the like or an inorganic oxide such as silica, etc. and the like on a film of such resins. In addition, the moisture impermeable layer 14 may be a single layer or a laminate of two or more layers, wherein each layer may be a foil or film made from a single material, or a foil or film comprised of a composition containing plural materials. While the thickness (total thickness) of the moisture impermeable layer 14 is not particularly limited, it is preferably 10-100 μm to afford the toughness and the easy-to-open property as a package of a patch.

A preferable embodiment of the moisture impermeable layer 14 includes one layer or a laminate of two or more layers selected from a metal layer such as aluminum and the like; a poly(ethylene terephthalate) (PET) layer, a high density polyethylene (HDPE) layer, a vinylidene chloride layer; and these resin layers each vapor deposited with a metal such as aluminum and the like or inorganic oxide such as silica, alumina and the like. With this embodiment, the moisture can be shut off at a strikingly high level.

When a packaging member is used for a patch that does not require shutting off of light with a particular wavelength, the first package 11 may be formed from a material transparent to the light with said wavelength. To stably retain the physiologically active ingredient in a patch, however, a constitution capable of shutting off the far-red light, infrared light and ultraviolet rays is preferable, and a constitution comprising at least a metal foil such as an aluminum foil and the like is preferable. Accordingly, in consideration of the intensity and utility of the moisture impermeable layer, a particularly preferable embodiment is a laminate of a PET film and an aluminum foil, most preferably a laminate of a PET film with 6-75 μm thickness and an aluminum foil with 6-90 μm thickness.

(Other Layer)

As mentioned above, the first package 11 basically has a laminate structure of acrylonitrile resin layer 12/moisture-absorbing layer 13/moisture impermeable layer 14. In addition to the above-mentioned layers, one or more layers can be laminated as necessary.

Figure 3:
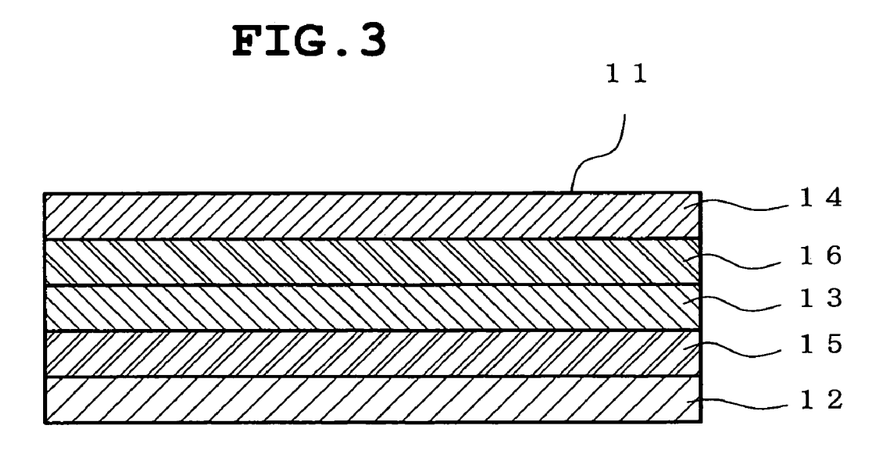
FIG. 3 is a schematic sectional view of an exemplary first package to be used in the present invention.

For example, as exemplarily shown in FIG. 3, a first intermediate layer 16 can be disposed between the moisture impermeable layer 14 and the moisture-absorbing layer 13. Examples of the first intermediate layer 16 include a cushioning layer providing cushioning performance between the moisture-absorbing layer 13 and the moisture impermeable layer 14. As the cushioning layer, a LDPE layer or a high density polyethylene (HDPE) layer is preferable, and the thickness is preferably 15-25 μm. The "high density polyethylene (HDPE)" in the present invention is a polyethylene having a specific gravity $\rho(g/cm^3)$ of not less than 0.94 and less than 0.96.

As exemplarily shown in FIG. 3, moreover, a second intermediate layer 15 can be disposed between the acrylonitrile resin layer 12 and the moisture-absorbing layer 13. A rapid decrease in the moisture content of a patch held in a packaging member may exert an undesirable effect on the quality of the patch, such as induced precipitation of a component in the adhesive layer, for example, the physiologically active ingredient, and the like. Thus, examples of such second intermediate layer 15 include moisture permeation control layer which controls the moisture permeation rate of the acrylonitrile resin layer 12. As the moisture permeation control layer, an LDPE layer is preferable, and the thickness is preferably 5-15 μm. Using such LDPE layer, degradation of the moisture absorbability of the first package during the production step of a patch package structure can be suppressed. In addition, a rapid decrease in the moisture content of a patch held in a packaging member can be reduced while ensuring the moisture permeability of the acrylonitrile resin layer 12.

Moreover, cellophane, paper and the like can be laminated on the outer side of the moisture impermeable layer 14 (i.e., the side of the moisture impermeable layer 14, which is opposite from the contact face with the moisture-absorbing layer 13) for the purpose of improving the attaching performance of printing ink used for printing indications and the like, improving slip property of the packaging member, suppressing deterioration of the packaging member due to friction and the like.

Examples of other layer that can be laminated include adhesive layer, colored layer, printed layer, vapor deposition layer, primer layer, surface protection layer (overcoat layer), adhesive layer and the like.

[Second Package]

In the present invention, the packaging member can be constituted with a second package in addition to the first package. The second package is not particularly limited as long as it has a sealable area at least on one surface thereof so that a packaging member can be formed by sealing with the first package. Accordingly, a package known per se, which is usable for the packaging member of a patch, can be used without any limitation. Examples thereof include resin films made of polyolefin (e.g., polyethylene, polypropylene and the like), polyester (e.g., poly(ethylene terephthalate) and the like), poly(vinyl chloride), polyacrylonitrile and the like; films obtained by vapor-deposing metal such as aluminum and the like, or inorganic oxide such as silica alumina and the like on the resin film; metal foils such as aluminum foil and the like, and the like. In addition, a laminate film laminated not less than optional two selected from these and the like can be mentioned. Particularly, for easy production of a packaging member, at least one surface preferably has a heat sealable layer constitution. An example of such package is a constitution free of a desiccant. Using a second package having a constitution free of a desiccant along with the first package, a package structure capable of stable retention of the physiologically active ingredient in a patch during preservation, which is the object of the present invention, while suppressing an increase in the thickness of the packaging member, can be provided.

In the present invention, moreover, a package having the same constitution as the first package can also be used for the second package. In this case, a packaging member capable of reducing the number of parts therein and more certainly achieving the aforementioned effect by the first package can be obtained.

[Laminate]

In the present invention, the method of laminating respective layers in the first package and the second package is not particularly limited, and a known method can be used. For example, a dry lamination method, an extrusion lamination method, a coextrusion method, a wet lamination method, a heat lamination method and the like can be employed.

[Packaging Member]

The packaging member of the present invention can be formed by processing only the first package. However, the first package and the second package are preferably combined to form a packaging member, since a patch can be easily packaged, the physiologically active ingredient can be stably maintained in the patch during preservation and a packaging member suitable for industrial continuous production can be obtained.

(Pouch-Like Packaging Member)

Figure 4:
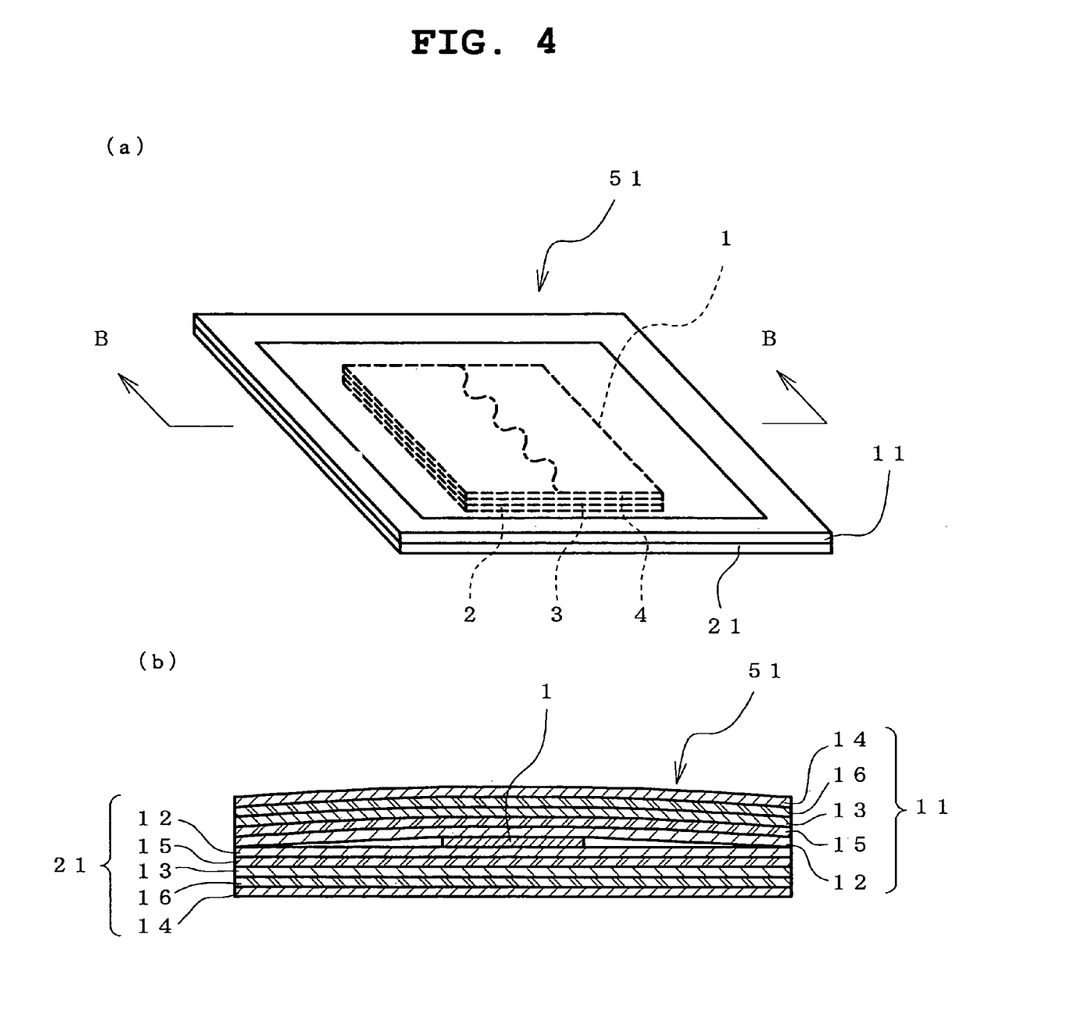

FIGS. 4(a) and 4(b) show one embodiment of the packaging member of the present invention. The packaging member 51 is a pouch-like packaging member, and as shown in FIG. 4(b), the acrylonitrile resin layer 12 in the first package 11 and a sealable surface (surface of the acrylonitrile resin layer 12 in this embodiment) of the second package 21 are directly faced with each other, a patch 1 is sandwiched between them, and each periphery thereof is sealed to give the member. Such pouch-like packaging member provides advantages such as easy production, a small thickness of the whole packaging member, good flexibility and good handling property of the packaging member per se and the like. In addition, since the first package 11 has rigidity and flexibility, it is suitable for such packaging member. In the present invention, the form of the pouch-like packaging member is not particularly limited, and may be a four-side seal bag as shown in FIG. 4, as well as, for example, a three-side seal bag, a gusset bag, a free-standing bag, a pillow bag and the like. The packaging member 51 shown in FIG. 4 comprises the first package 11 and the second package 21, which are substantially flat planes, where the first package 11 and the second package 21 are free of a shoulder and a folded part. Thus, a packaging member comprising the first package 11 and the second package 21, which are both substantially flat planes, is more advantageous for stable retention of the physiologically active ingredient, since it is free of an adverse influence, which is caused by a damage on the layer(s) due to bending of the package, on the permeability and impermeability of moisture, the physiologically active ingredient and the like in the packaging member.

(Blister-Like Packaging Member)

Figure 5:
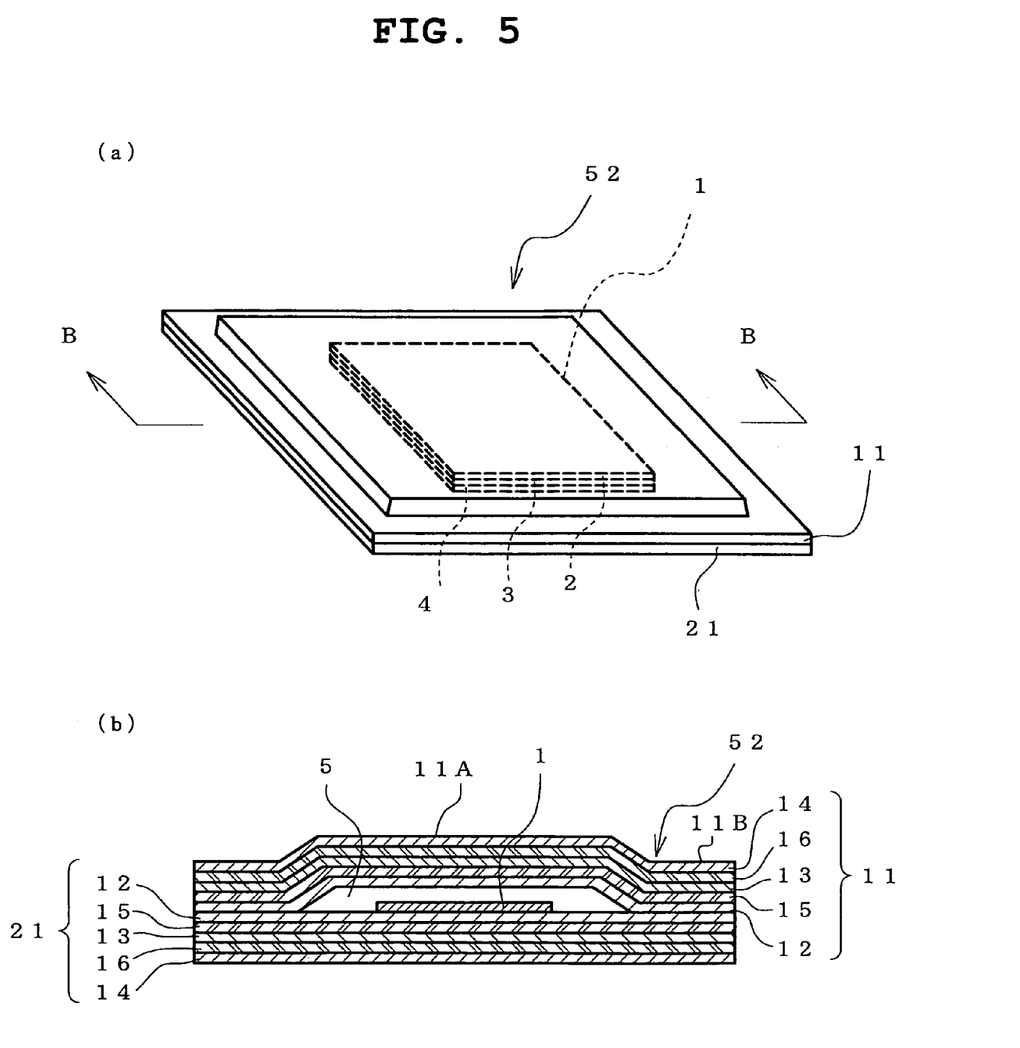

FIGS. 5(a) and 5(b) show a packaging member 52, which is another embodiment of the packaging member of the present invention. In the present invention, when the packaging member is formed by a first package 11 and a second package 21, one or both of the first package 11 and the second package 21 is/are formed in a container shape (with a pocket), as shown in the packaging member 52 of such embodiment, which is what is called a blister-like packaging member. In this type of blister-like packaging member, since a space 5 is ensured in the periphery of patch 1 inside the packaging member, as shown in FIG. 5(b), patch 1 is not easily subject to a pressure from the outside of the packaging member. Thus, the packaging member is less likely to suffer from sticking out or flow of the adhesive layer from the peripheral portion of a patch, which causes attachment of the adhesive to the inside of the packaging member, thereby making it difficult to take out the patch from the packaging member after unsealing the same.

On the other hand, when a blister-like packaging member ensuring a space around the contents is used for packaging a patch, the component in the patch, such as a physiologically active ingredient, generally tends to decrease with ease due to the comparatively large volume of the space in the packaging member. However, a package structure comprising the particular package of the present invention (i.e., package having a laminate structure of acrylonitrile resin layer/moisture-absorbing layer/moisture impermeable layer) can suppress a content decrease of the component in the patch even when a blister-like packaging member is formed. Thus, the blister-like packaging member can be advantageously practiced. In the case of a blister-like packaging member, moreover, a package formed in a container shape can have a large surface area of the package surrounding the patch by changing the size and shape of the pocket. Thus, it is advantageous in that the moisture absorbability of the package can be arbitrarily controlled by changing the size of the pocket.

In the present invention, the blister-like packaging member may contain the first package formed in a container form or the second package formed in a container form. In the packaging member 52 in FIG. 5, the first package 11 has a pocket 11A approximately in the center thereof, the second package 21 is a sheet and, as shown in FIG. 5(b), the acrylonitrile resin layer 12 of the first package 11 and the acrylonitrile resin layer 12 of the second package 21 are directly faced with each other, patch 1 is held in a pocket 11A in the first package 11, a non-pocket part 11B in the first package 11 and the periphery of the second package 21 directly facing therewith are heat sealed to give a packaging member. The second package 21 in the packaging member 52 of this embodiment has a moisture-absorbing layer as in the first package.

When a blister-like packaging member is formed using, as the second package, a package without a moisture-absorbing layer, the first package is preferably used in the form of a sheet and the second package is preferably formed into a container. In this way, the production is facilitated since the second package is flexible without a moisture-absorbing layer. Alternatively, it is also preferable to use the second package in the form of a sheet and form the first package into a container. This is advantageous since the possibility of damage to the patch held in the packaging member becomes small because the first package has rigidity of a packaging member for a patch due to the presence of a moisture-absorbing layer and an acrylonitrile resin layer.

In the package structure of the present invention, the package and the patch may have any shape, for example, an approximately polygonal flat shape such as about square, about rectangle and the like, circle, ellipse and the like.

The present invention is explained in more detail in the following by referring to Examples and Comparative Examples, which are not to be construed as limitative.

In the following description, "parts" means "parts by weight". In addition, the abbreviations mean the following.

PET: poly(ethylene terephthalate)

AL: aluminum

The moisture permeation rate of the laminate of 12 μm-thick PET film/9 μm-thick AL foil is 0.02 g/m$^2$/24 hr.

LDPE: low density polyethylene water-absorbing layer A: layer containing 70 wt % LDPE+ 30 wt % MgSO$_4$ MgSO$_4$: magnesium sulfate powder (average particle size: 5 μm)

PAN: polyacrylonitrile resin (copolymer of 67 wt % acrylonitrile/7 wt % butadiene/26 wt % methyl acrylate, moisture permeation rate of 30 μm-thick PAN film is 70 g/m$^2$/24 hr)

[Preparation of Patch]

2-Ethylhexyl acrylate (72 parts), N-vinyl-2-pyrrolidone (25 parts) and acrylic acid (3 parts) were copolymerized in ethyl acetate under an inert gas atmosphere to give an acrylic acid ester polymer solution. Ethyl acetate was further added to the polymer solution to adjust the viscosity. Then, the obtained viscous solution was applied to a 75 μm-thick polyester liner such that the thickness after drying was 60 μm, and dried to form an adhesive layer.

As a support, a laminate of a 2 μm-thick polyester film laminated on a polyester non-woven fabric (12 g/m$^2$) was prepared, and a non-woven fabric surface of the laminate was adhered to the above-mentioned adhesive layer. The obtained laminate was cut out in a 32 mm×32 mm about rectangle to give a patch. The weight of the adhesive layer of the patch was 60 mg.

[Preparation of Patch Containing a Physiologically Active Ingredient]

The acrylic acid ester polymer solution obtained in the above-mentioned [Preparation of patch] was mixed with scopolamine in an amount of 10 parts relative to 90 parts of the solid content of the acrylic acid ester polymer, and ethyl acetate was further added to control the viscosity. The obtained viscous solution was applied to a 75 μm-thick polyester liner such that the thickness after drying was 100 μM, and dried to form an adhesive layer containing a physiologically active ingredient.

As a support, a laminate of a 2 μm-thick polyester film laminated on a polyester non-woven fabric (12 g/m$^2$) was prepared, and a non-woven fabric surface of the laminate was adhered to the above-mentioned adhesive layer. The obtained laminate was cut out in a 32 mm×32 mm about rectangle to give a patch. The weight of the adhesive layer of the patch was 100 mg.

Example 1

A sheet was produced by laminating 12 μm-thick PET film/9 μm-thick AL foil/20 μm-thick LDPE film/30 μm-thick water-absorbing layer A/10 μm-thick LDPE film/30 μm-thick PAN film by dry lamination. The 20 μm-thick LDPE film/30 μm-thick water-absorbing layer A/10 μm-thick LDPE film was laminated by coextrusion inflation.

The sheet was cut into a 65 mm×65 mm about rectangle to give a first package. Similarly, moreover, the sheet was cut into a 65 mm×65 mm about rectangle to give a second package. The PAN surfaces of the first package and the second package were directly faced against each other, the patch prepared above, which was free of a physiologically active ingredient, was placed approximately in the center between them, and the periphery of each package was heat sealed such that the packages were substantially flat planes to give a patch package structure shown in FIG. 4.

Comparative Example 1

In the same manner as in Example 1 except that a sheet free of 20 μm-thick LDPE film/30 μm-thick water-absorbing layer A/10 μm-thick LDPE film was used for the first package and the second package, a patch package structure was completed.

Example 2

In the same manner as in Example 1 except that a sheet free of 20 μm-thick LDPE film/30 μm-thick water-absorbing layer A/10 μm-thick LDPE film was used for the second package, a patch package structure was completed.

Comparative Example 2

In the same manner as in Example 1 except that a sheet free of PAN film (acrylonitrile resin layer) was used for the first package and the second package, a patch package structure was completed.

Example 3

As the first package, the first package produced in Example 1 was prepared. Separately, a sheet was obtained by laminating 12 μm-thick PET film/80 μm-thick AL foil/30 μm-thick PAN film by dry lamination, a pocket was formed on the PAN film side, and the sheet was processed into a 65 mm×65 mm (flat plane size) about rectangle to give a second package container. A patch was placed in a pocket of the second package container, the aforementioned first package was placed as a lid on the second package such that the PAN film came closer to the patch, and the periphery thereof and the non-pocket part (periphery) of the second package were heat sealed to complete a patch package structure. Such patch package structure is different from the embodiment shown in FIG. 4, since the second package is a container and the first package is a sheet (flat plane).

Comparative Example 3

In the same manner as in Example 3 except that a sheet obtained by laminating a 12 μm-thick PET film/80 μm-thick AL foil/30 μm-thick PAN film on the first package by dry lamination was used as the first package, a patch package structure was completed.

Example 4

In the same manner as in Example 1 except that a patch containing a physiologically active ingredient was used as the patch, a patch package structure was completed.

Comparative Example 4

In the same manner as in Comparative Example 1 except that a patch containing a physiologically active ingredient was used as the patch, a patch package structure was completed.

Comparative Example 5

In the same manner as in Comparative Example 2 except that a patch containing a physiologically active ingredient was used as the patch, a patch package structure was completed.

Example 5

In the same manner as in Example 3 except that a patch containing a physiologically active ingredient was used as the patch, a patch package structure was completed.

Experimental Example 1

The moisture concentration of the patch in the patch package structures of Examples 1 to 3 and Comparative Examples 1 to 3 was measured immediately after production. In addition, the patch package structures were preserved under the conditions of 40° C., relative humidity 75% for 1 month and the moisture concentration of the patch was measured in the same manner. The measurement method of the moisture concentration of the patch was as follows.

[Measurement Method of Moisture Concentration of Patch]

A liner was detached from a patch and the patch was weighed, placed in a moisture vaporization apparatus, and heated to vaporize the moisture in the patch. The moisture was introduced using a nitrogen gas into a moisture measurement apparatus, and the amount of moisture was measured by the Karl Fischer coulometric titration method. The weight of the support was subtracted from the weight of the patch to give the weight of the adhesive layer. The weight of the moisture was divided by the weight of the adhesive layer to give a moisture concentration (ppm).

The results are shown in Table 1.

Experimental Example 2

The content (mg) of the physiologically active ingredient of the patch package structures of Examples 4 and 5 and Comparative Examples 4 and 5 was measured per one patch containing the physiologically active ingredient immediately after production. Then, the patch package structures were preserved under the conditions of 40° C., relative humidity 75% for 2 months and the content (mg) of the physiologically active ingredient after the preservation was measured in the same manner. The measurement method of the content (mg) of the physiologically active ingredient was as follows.

[Measurement Method of the Content of Physiologically Active Ingredient in Patch]

A liner was detached from a test preparation and the preparation was extracted with methanol. The extract was analyzed by high performance liquid chromatography to determine the content (mg) of the physiologically active ingredient.

The results are shown in Table 1.

TABLE 1

| | moisture concentration (ppm) after preservation | (moisture concentration after preservation/moisture concentration immediately after production) × 100 (%) |
|---|---|---|
| Ex. 1 | 2580 | 85 |
| Com. Ex. 1 | 3515 | 116 |
| Ex. 2 | 2726 | 90 |
| Ex. 3 | 2758 | 91 |
| Com. Ex. 2 | 2640 | 86 |
| Com. Ex. 3 | 3367 | 111 |

TABLE 2

| | (content of physiologically active ingredient after preservation/content of physiologically active ingredient immediately after production) × 100 (%) |
|---|---|
| Ex. 4 | 99 |
| Com. Ex. 4 | 90 |
| Ex. 5 | 98 |
| Com. Ex. 5 | 95 |

As is clear from Table 1, in Example 1 using the first package and the second package both containing an acrylonitrile resin layer and a moisture-absorbing layer, the moisture concentration of the patch decreased markedly. In Example 2, moreover, although a package free of a moisture-absorbing layer was used as the second package, the moisture concentration of the patch decreased more than the arithmetic average of Example 1 and Comparative Example 1 using the first package and the second package both free of a moisture-absorbing layer. This is an unpredictable advantageous effect. The same tendency as between Examples 1, 2 and Comparative Example 1 was found between Example 3 and Comparative Example 3 wherein blister-like packaging members were prepared. In Comparative Example 2 wherein the first package and the second package both had a moisture-absorbing layer but were free of an acrylonitrile resin layer, the moisture concentration was the same as in Example 1, but when pressed with a hand, the packaging member showed low rigidity and insufficient impact resistance of the patch was feared.

As is clear from Table 2, as for the patch containing a physiologically active ingredient, Example 4 wherein both the first package and the second package had an acrylonitrile resin layer and a moisture-absorbing layer hardly showed a decrease in the content of the physiologically active ingredient even after preservation. In addition, in Example 5 wherein a blister-like packaging member was formed, a decrease in the content of the physiologically active ingredient was hardly observed even after preservation, as in Example 4. In contrast, in Comparative Example 4 wherein the first package and the second package were both free of a moisture-absorbing layer, the content of the physiologically active ingredient decreased markedly after preservation, and in Comparative Example 5 wherein the first package and the second package both had a moisture-absorbing layer but free of an acrylonitrile resin layer, the content of the physiologically active ingredient decreased after preservation. The patch of Example 4 hardly showed a decrease in the content of the physiologically active ingredient even after preservation. Thus, it is strongly suggested that the adsorbability of the physiologically active ingredient in the acrylonitrile resin layer was low, and the moisture concentration of the patch of Example 4 remarkably decreased as in the patch of Example 1 due to preservation.

From the foregoing, since the patch package structure of the present invention showed a remarkably decreased moisture concentration of the patch after preservation, it is clear that the moisture in the patch decreases due to preservation. It is also clear that a patch containing a physiologically active ingredient shows a suppressed decrease in the content of the physiologically active ingredient in the patch after preservation. Therefore, the patch package structure of the present invention wherein the patch contains a physiologically active ingredient strongly suggests that the decomposition of the physiologically active ingredient due to preservation can be suppressed, and a patch stably retaining the physiologically active ingredient even after preservation can be provided.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2007-323891 filed in Japan, the contents of which are incorporated in full herein by this reference.

The invention claimed is:

1. A patch package structure comprising a patch and a packaging member housing the patch,
wherein
the patch comprises a physiologically active ingredient, a support and an adhesive layer formed on at least one surface of the support,
the packaging member comprises a first package,
the first package comprises an acrylonitrile resin layer, a first low density polyethylene layer formed on the acrylonitrile resin layer, a moisture-absorbing layer which comprises a composition containing a moisture-absorbing agent and a polyolefin resin formed on the first low density polyethylene layer wherein the content of the moisture-absorbing agent is 15-60 weight percent relative to the total weight of the composition, a second low density polyethylene layer formed on the moisture-absorbing layer, and a moisture impermeable layer formed on the second low density polyethylene layer, and
the acrylonitrile resin layer is provided on the proximal side of the patch.

2. The patch package structure of claim 1, wherein the packaging member further comprises a second package, one of the first package and the second package is in the form of a tray, and the other is in the form of a sheet.

3. The patch package structure of claim 1, wherein the packaging member further comprises a second package, and both the first package and the second package are each in the form of a sheet.

4. The patch package structure of claim 1, wherein the acrylonitrile resin is a copolymer comprising acrylonitrile as a main structural unit.

5. The patch package structure of claim 4, wherein the copolymer comprising acrylonitrile as a main structural unit is a copolymer comprising, as structural units, at least acrylonitrile and alkyl(meth)acrylate wherein the alkyl of the alkyl(meth)acrylate has 1 to 6 carbon atoms.

6. The patch package structure of claim 4, wherein the copolymer comprising acrylonitrile as a main structural unit is a copolymer comprising at least acrylonitrile and butadiene as structural units.

7. The patch package structure of claim 4, wherein the copolymer comprising acrylonitrile as a main structural unit is a copolymer comprising, as structural units, acrylonitrile, butadiene, and alkyl(meth)acrylate wherein the alkyl of the alkyl (meth)acrylate has 1 to 6 carbon atoms.

8. The patch package structure of claim 3, wherein the first package and the second package are substantially flat.

9. The patch package structure of claim 2, wherein
the second package comprises an acrylonitrile resin layer, a moisture-absorbing layer which comprises a composition containing a moisture-absorbing agent formed on the acrylonitrile resin layer wherein the content of the moisture-absorbing agent is 15-60 weight percent relative to the total weight of the composition, and a moisture impermeable layer formed on the moisture-absorbing layer, and
the acrylonitrile resin layer is provided on the proximal side of the patch.

10. The patch package structure of claim 9, wherein the second package further comprises a moisture permeation control layer between the acrylonitrile resin layer and the moisture-absorbing layer.

11. The patch package structure of claim 9, wherein the acrylonitrile resin is a copolymer comprising acrylonitrile as a main structural unit.

12. The patch package structure of claim 9, wherein the copolymer comprising acrylonitrile as a main structural unit is a copolymer comprising, as structural units, at least acrylonitrile and alkyl(meth)acrylate wherein the alkyl of the alkyl(meth)acrylate has 1 to 6 carbon atoms.

13. The patch package structure of claim 9, wherein the copolymer comprising acrylonitrile as a main structural unit is a copolymer comprising at least acrylonitrile and butadiene as structural units.

14. The patch package structure of claim 9, wherein the copolymer comprising acrylonitrile as a main structural unit is a copolymer comprising, as structural units, acrylonitrile, butadiene, and alkyl(meth)acrylate wherein the alkyl of the alkyl (meth)acrylate has 1 to 6 carbon atoms.

15. The patch package structure of claim 3, wherein
the second package comprises an acrylonitrile resin layer, a moisture-absorbing layer which comprises a composition containing a moisture-absorbing agent formed on the acrylonitrile resin layer wherein the content of the moisture-absorbing agent is 15-60 weight percent relative to the total weight of the composition, and a moisture impermeable layer formed on the moisture-absorbing layer, and
the acrylonitrile resin layer is provided on the proximal side of the patch.

16. The patch package structure of claim 2, wherein the second package comprises an acrylonitrile resin layer, and the acrylonitrile resin layer is provided on the proximal side of the patch.

* * * * *